United States Patent [19]
Schlager

[11] 4,186,748
[45] Feb. 5, 1980

[54] THERMOGRAPHIC APPARATUS FOR PHYSICAL EXAMINATION OF PATIENTS

[76] Inventor: Kenneth J. Schlager, 12825 Elmwood Rd., Elm Grove, Wis. 53122

[21] Appl. No.: 875,527

[22] Filed: Feb. 6, 1978

[51] Int. Cl.² ............................................. A61B 5/00
[52] U.S. Cl. ............................... 128/736; 73/359 R; 73/343.5; 364/415
[58] Field of Search .............. 128/2 H, 2 A, 664, 736; 358/113; 250/342, 359 R; 73/343.5 R, 355 R, 339 R, 341; 364/415, 557

[56] References Cited
U.S. PATENT DOCUMENTS

| | | | |
|---|---|---|---|
| 2,804,069 | 8/1957 | Schwamm et al. | 128/2 A |
| 3,459,925 | 8/1969 | Goosey et al. | 73/341 |
| 3,622,784 | 11/1971 | DelGuercio | 128/2.1 R |
| 3,699,813 | 10/1972 | Lamb | 73/343.5 |
| 3,854,336 | 12/1974 | Bibby | 73/351 |
| 3,970,074 | 7/1976 | Mogos et al. | 128/2 H |
| 4,114,442 | 9/1978 | Pratt | 73/341 |
| 4,122,720 | 10/1978 | Podl | 73/346 |

OTHER PUBLICATIONS

*Micro—Processors Enhance Thermograms to Aid Diagnosis of Breast Tumors,* in *Electronics,* vol. 49, No. 14, p. 8E, Jul. 8, 1976.

Szeles, D., *Biothermography in the 8-to 14 -Micron Spectral Region,* Proc. 7th Ann. Biomed. Sci. Instr. Symp. on Imag. in Med., Ann Arbor, Mich., 19-22, May 1969, pp. 23-29.

Ring, E. F. et al., *Thermography in Rheumatic Diseases,* AGA Corp. Publication No. 556-089, Oct. 1973.

Gilbert, B. K. et al., *A Real-Time Hardware System for Digital Processing of Wideband Video Images,* IEEE Trans. on Computers, vol. C-25, No. 11, pp. 1089-1100, Nov. 1976.

*Primary Examiner*—Robert W. Michell
*Assistant Examiner*—Francis J. Jaworski
*Attorney, Agent, or Firm*—Andrus, Sceales, Starke & Sawall

[57] ABSTRACT

A passive thermographic analytical apparatus for determining the presence of cancer includes a left and right breast scanner array, each of which includes a matrix of infra-red energy sensors and reflectors mounted in a close spaced array for producing a pattern of temperature measurements. The arrays are mounted within an adjustable support to permit spatial positioning and alignment of the arrays. Each sensor produces an analog voltage proportional to the body temperature. The sensor output voltages are sequentially read and converted into appropriate digital form for storage in a RAM memory of a microprocessor, which includes a pattern recognition program to directly create an automated diagnosis of the radiation pattern from which the normality or abnormality of the breasts can be diagnosed. The various parameters are reduced to a multiple digit number which is displayed. The number is encoded to a particular condition.

11 Claims, 7 Drawing Figures

THERMOGRAPHIC APPARATUS FOR PHYSICAL EXAMINATION OF PATIENTS

BACKGROUND OF THE INVENTION

This invention relates to the thermographic apparatus for physical examination of a patient by directly measuring and analyzing the thermal radiation patterns of a patient's body.

Thermographic apparatus has been suggested for a number of years for analyzing the biological condition of human patients and the like. Such apparatus has recently more particularly been applied to the early detection of cancer and particularly breast cancer in female patients. Although there are variations in thermal radiation patterns of patients, recent developments and application of computers have allowed statistical analysis which produces accurate separation between healthy and possibly cancerous patients. One satisfactory computer-based system is more fully disclosed in a paper presented in the May 1975 issue of RADIOLOGY, Vol. 115, No. 2, at pages 341-347, in an article entitled "Computer Diagnosis of Breast Thermograms" by Marvin C. Ziskin, M.D., et al. A thermographic technique is discussed employing the photographing of the breast area and then scanning the photograph to develop a digitized image frame. A conventional close circuit television camera is used to produce a point by point reading of the thermal conditions, with digitizing of each point. Generally each scan line includes 192 points and two hundred and fifty-six scan lines are used to create a dimensional array in excess of four thousand points. These numbers are stored and subsequently processed by a general purpose computer. The decision algorithm employs a standard statistical technique of discrimination analysis in which a statistical standard is determined and various comparisons and thresholds are checked from which a determination of normality and abnormality is made. Although such diagnostic apparatus has been developed to the point where practical results are obtained, an apparatus such as disclosed is relatively complex and costly, which would significantly limit the application and usage of such a computerized thermographic system. Generally, only relatively large hospitals would have a sufficient usage factor to justify the cost. There therefore remains a need for a low cost computer-based thermographic screening apparatus.

SUMMARY OF THE PRESENT INVENTION

The present invention is particularly directed to a passive thermographic analytical apparatus which is relatively inexpensive and provides a direct readout of the results of the analysis of the thermographic radiation pattern of the human body. Generally, in accordance with the present invention a multiplicity of energy sensors such infra-red radiation are mounted in a close spaced array for producing a plurality of measurements of the aligned areas of the body. The sensor array is mounted within an adjustable support to permit spatial positioning of the array in accordance with the individual patient. The multiplicity of the sensors are simultaneously or sequentially read to develop related analog signals which are converted into appropriate digital form and stored in a memory means for processing. Although any suitable hardwired system could be employed, a microprocessor is preferably employed to process the multiplicity of signals in accordance with particular pattern recognition programs to directly provide an automated diagnosis of the human radiation pattern. In accordance with one aspect of the present invention, the instrument analysis is reduced to an encoded readout, such as a numeric readout which is suitably encoded to a particular condition. Thus, in operation, the patient merely steps in front of the scanning array apparatus, which rapidly and practically instantaneously scans the aligned breasts and develops digital numbers which are processed by statistical pattern recognition programs such as disclosed in the previously referenced article.

In a preferred and particularly novel arrangement a pair of separate scanning arrays are provided each consisting of a matrix of thermal sensitive sensing elements such as thermopile devices which produce an output voltage proportional to the temperature of the thermopile junction, and associated optical devices for collecting of the infra-red radiation in the aligned area and concentrating such energy upon the sensor sensing elements. In addition, one or more sensor elements are located between the two arrays for developing a reference temperature against which to compare the output numbers of the array. The two arrays are mounted for separate vertical positioning and for relative horizontal positioning for alignment with different patients.

Thermopile devices or the like are readily provided which have a very rapid response to the energy input, and the output numbers can be simultaneously or sequentially stored in a simple rapid manner for subsequent analysis in a resident hardwired or programmed instrument such as a micro-processor.

Thus, the present invention provides a simple, reliable and relatively inexpensive thermographic system or instrument for directly producing an encoded output indicative of the conditions monitored. The invention thus provides a low cost, screening instrument for breast cancer, and the like.

BRIEF DESCRIPTION OF THE DRAWINGS

The drawings furnished herewith illustrate a preferred embodiment of the present invention in which the above advantages and features are clearly disclosed as well as other which will be readily understood by those skilled in the art.

In the drawings.

DESCRIPTION OF THE ILLUSTRATED EMBODIMENT

Figure 1:
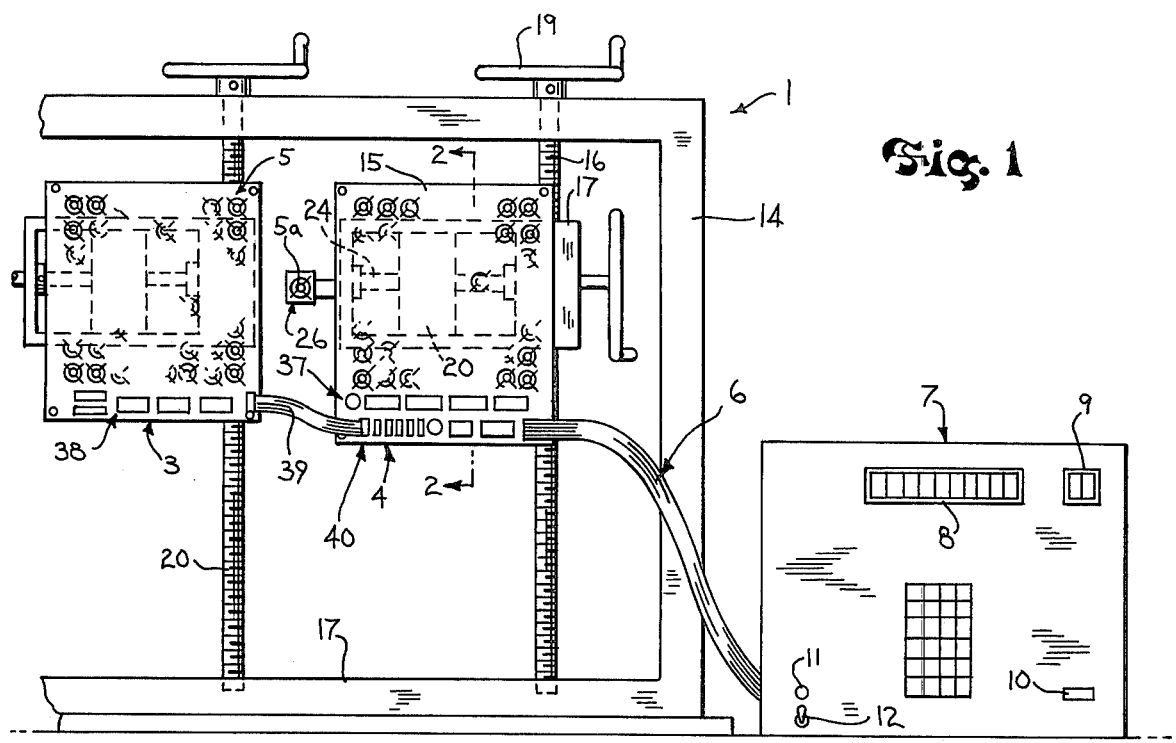
FIG. 1 is a front elevation view of the scanning apparatus and inter-related data processing control unit constructed in accordance with the present invention.
Figure 2:
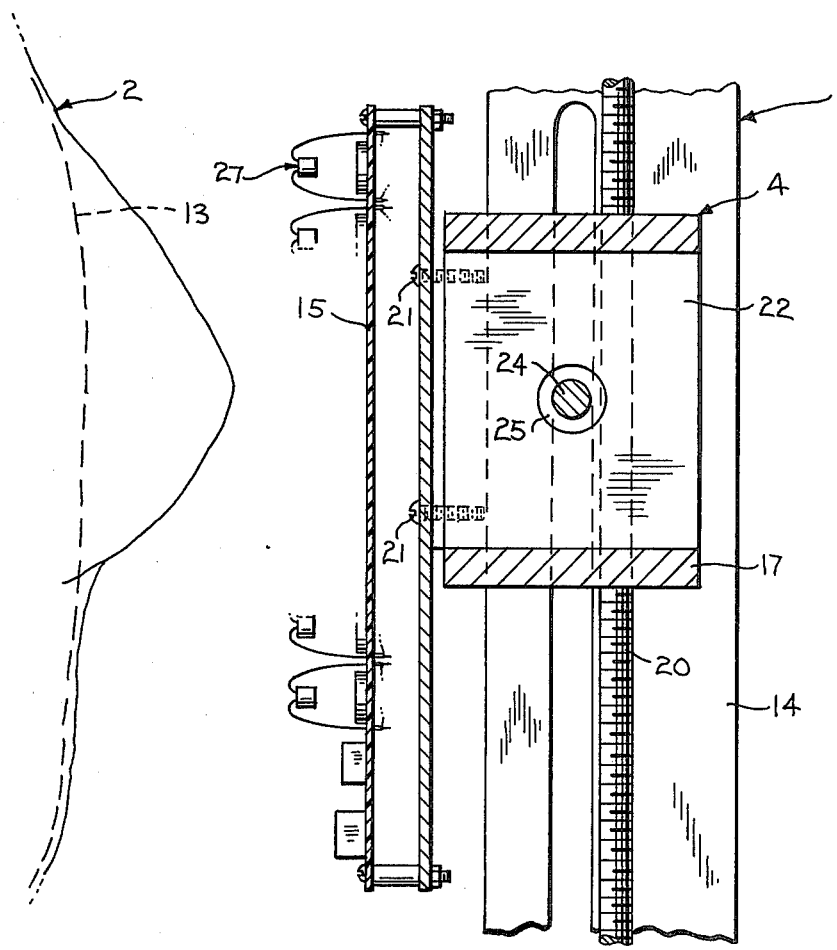
FIG. 2 is an enlarged vertical section through an array unit shown in FIG. 1.
Figure 3:
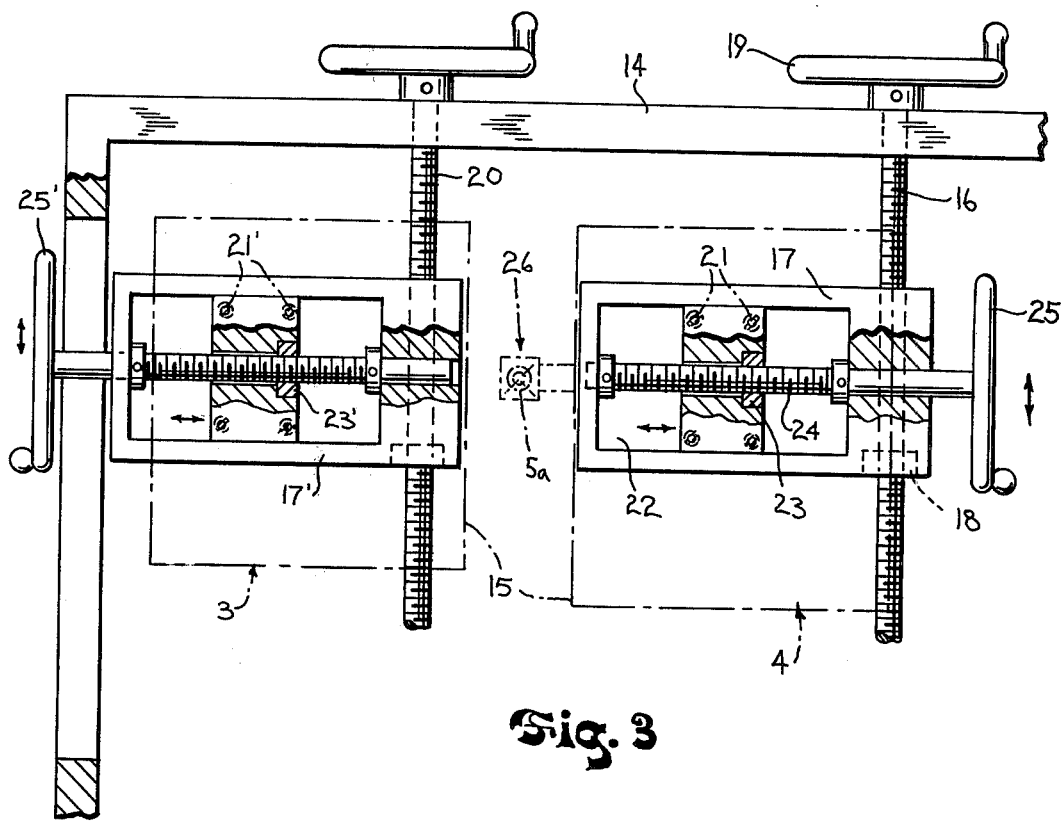
FIG. 3 is a rear view of the apparatus shown in FIG. 1 and illustrating a suitable positioning apparatus.

Referring to the drawings and particularly to FIGS. 1 through 3, a breast cancer thermographic diagnostic apparatus is shown including a breast scanning unit 1 adapted to be mounted in relatively fixed relationship with respect to a patient 2. The apparatus includes first and second similar thermal measurement array units 3 and 4 which are adjustably mounted for selective and precise alignment with the breast of the patient 2. Each array unit 3 and 4 consists of a selected matrix or arrangement of individual similar temperature sensitive assemblies 5 such as assemblies which are responsive to the infrared radiation from the body of the patient and particularly responsive to the aligned portion of the breasts as more fully developed hereinafter. A reference temperature assembly 5a is located between the array units 3 and 4. The output of the scanning unit 1 is coupled by a suitable power and signal cable 6 to an analyzing and display module 7. In a preferred embodiment, the module 7 is a microprocessor-based system such as disclosed more fully in FIGS. 6 and 7 and hereinafter discussed. Generally, the module 7 includes means to convert the output of the individual sensing assembly 5 into an appropriate digital number which is subsequently processed by the module 7 through a series of pattern recognition programs in order to establish a positive or negative cancer diagnosis. The output of the analysis is presented in a digital manner on a numeric readout 8 on the front of the module 7. A significant factor in the analysis is the patient's age. A numeric input means shown as a pair of thumbwheels 9 is provided for the age entry. Other conventional controls such as a power switch buttom 10 and on-off lamp 11 and the like may also be provided. A start-reset key 12 is provided for initiating a diagnostic cycle.

In operation of the apparatus, the patient 2 is located in front of the scanner apparatus 1. The scanning array units 3 and 4 are properly located with respect to the particular patient. The start key 12 is actuated and the thermal radiation pattern of the right and left breasts as well as the temperature of the sternal region 13 between the two breasts is read. The output of the array units 3 and 4 is a corresponding series of voltage signals which are individually and directly related to the average temperature of the breast portions aligned with the temperature sensitive assemblies 5. The temperature-related voltages are converted to a digital form and then processed by the microprocessor through the pattern recognition program to produce the positive or negative breast cancer diagnosis. The processor is programmed to directly indicate by a numeric reading on the display 8 of the computer module 7 an indication of normality or abnormality. This reading may also indicate the degree of certainty of the diagnosis.

More particularly, in the illustrated embodiment of the present invention, the scanner apparatus 1 includes a rectangular frame 14 within which units 3 and 4 are mounted. Each of the array units 3 and 4 includes an 8×8 matrix of temperature sensitive assemblies 5. The assemblies 5 are arranged in well known columns and rows to define a square matrix, although any other matrix arrangement can of course be employed. Each unit 3 and 4 is similarly constructed, and includes a support board 15 which is mounted for vertical and horizontal movement as most clearly illustrated in FIGS. 1 and 3. Referring to array unit 4, a vertically oriented positioning bolt or shaft 16 is rotatably supported within the top and bottom legs of the frame 14. A support plate 17 includes a threaded nut portion 18 threaded onto the threaded shaft 16. A hand wheel 19 is secured on the upper end of bolt 16 for vertical positoning of plate 17. The board 15 is affixed to a sliding block 20 as by screws 21. The block 20 is located within a recess opening 22 in the support plate 17. The block 20 includes a threaded opening, shown as a nut 23, for receiving a laterally positioned threaded shaft 24 which is rotatably journaled at the opposite ends in the plate 17. Rotation of the shaft 24 therefore provides lateral positioning of the block 20 and attached array unit 4 within the rectangular opening 22. A handwheel 25 permits convenient horizontal positioning of the unit 4. The array unit 3 is similarly supported for vertical and horizontal positioning, and corresponding elements are identified by corresponding primed numbers.

In addition, a reference cell unit 26, which may consist of a single assembly 5 is located between array units 3 and 4. The location of unit 26 is not critical and the unit 26 may conveniently be attached to either of the units 3 and 4 for relative movement therewith or the frame 14 and may provide for adjustment in the positioning relative to units 3 and/or 4. The unit 26 is shown attached to unit 4 for purposes of illustration.

Any other adjustable positioning can be provided for the individual array units, which may of course include similar or other means for the individual vertical and horizontal movements of the left and right arrays.

Figure 4:
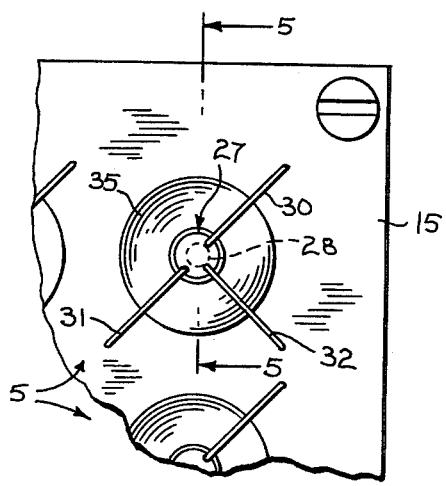
FIG. 4 is a fragmentary enlarged view of a portion of FIG. 1 for clearly illustrating details of the thermal sensor assembly.
Figure 5:
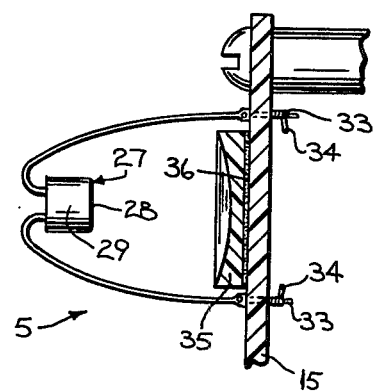
FIG. 5 is a fragmentary vertical section taken generally on line 5—5 of FIG. 4.

As previously noted, each of the illustrated array units 3 and 4 is similarly constructed and each similarly supports individual sensing assemblies 5, a preferred embodiment of which is more clearly shown in FIGS. 2, 4 and 5; and one unit 5 as shown in FIGS. 4 and 5 is particularly described. The assembly 5 includes a thermal sensitive element or device 27 which is a relatively small, compact element having a diameter smaller than the area to be scanned by the measurement device. A particularly satisfactory device is a thermopile measurement device of type S15 manufactured and sold by Sensors, Inc. The S15 device is a multiple-junction thin-film thermopile construction having an exposed active area 28 on one end. The device 27 generally includes a cylindrical housing 29 of approximately one-half inch or 10 millimeter diameter and having a pair of positive and negative connecting leads 30 and 31 and a case support wire 32 secured to the outer or base of the housing. The active area 28 is exposed through an opening in the opposite end of the housing 29 and is on the order of 1.5 millimeters square. The active area of the sensor in such a unit is generally constructed as more fully disclosed in U.S. Pat. No. 3,715,288.

As most clearly shown in FIG. 5, the sensor is mounted with the active area 28 facing the board 15, by bending of the three leads 30–32 back about the exterior of the casing 29. The leads 30–32 are suitably secured to pin elements 33 embedded in the array board 15. The positive and negative leads 30 and 31 are secured to terminal pins 33 which extend through the board 15 with the opposite ends interconnected to circuit leads 34 for interconnecting of the thermopile 28 into the appropriate circuit as hereinafter described.

The active area 28 is aligned with the center of a small convex mirror 35 which is secured or firmly affixed to the board 15 by a suitable adhesive 36 or the like. The mirror 35 is substantially larger than the sensing element 27 and collects the infrared radiation from the aligned breast portion and concentrates such energy upon the active area 28 of the element 27. The output voltage of the element 27 is a voltage proportional to the average termperature of the aligned portion of the breast.

The mirror may be formed of suitable acrylic material having a highly polished mirror surface to collect and reflect the energy onto the active area 28. Such mirrored devices can be readily provided by those skilled in the art and no further description thereof is given.

The output of the several sensing assemblies 5 and 5a are individually interconnected to the module 7 through any suitable terminal means 37 and 38 shown provided on the lower end of circuit boards 15. Thus, in the illustrated embodiment of the invention, a suitable multiple lead cable strip 39 interconnects the terminal means 38 to a coupling interface circuit means 40 at the lower end of the circuit board 15 of the unit 4, with the terminal means 37 of unit 4 interconnecting to the means 40. The output is connected by cable 6, which is also a multiple lead connecting strip, to the computer module 7.

Figure 6:
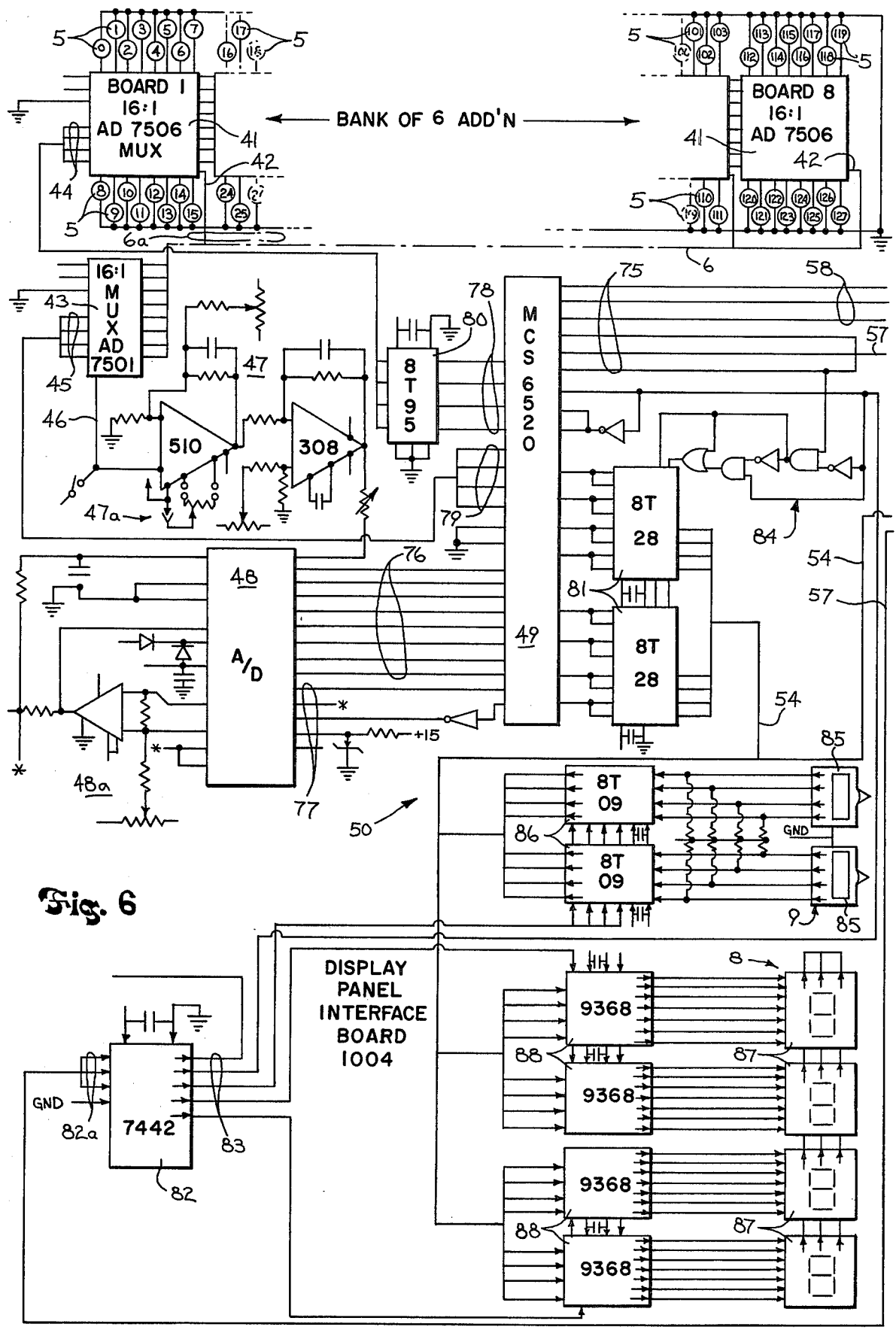
FIGS. 6 and 7 are a schematic electronic circuit used to multiplex, amplify and process the output of the sensing arrays illustrated on FIGS. 1-5.
Figure 7:
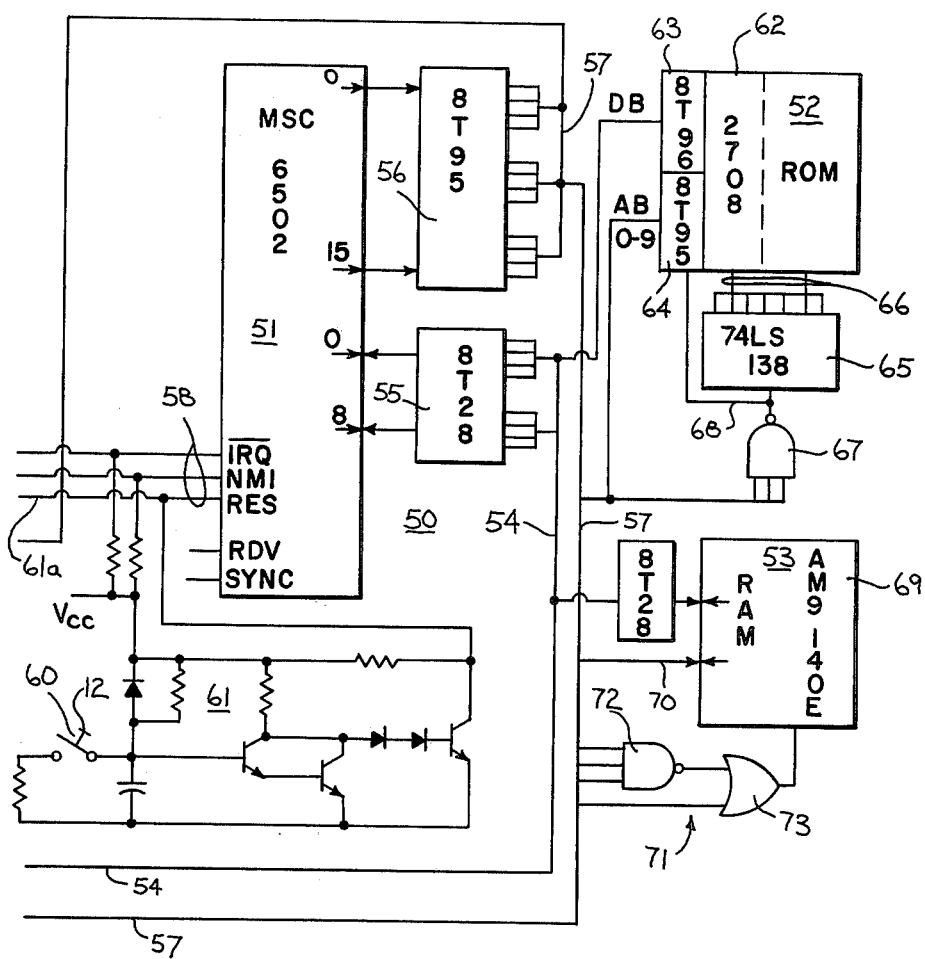

The computer module 7 may be of any suitable construction and a preferred structure is shown in FIG. 6, for purposes of clearly describing the invention.

Referring particularly to FIG. 6, the individual sensors are shown divided into groups of 16, each group being coupled to an individual 16×1 multiplexing circuit board 41. The sensing assemblies 5 thus produce eight different circuits 41, with the eight output lines 42 connected as the input to a 16×1 multiplexer 43. Each multiplexer 41 is similarly constructed with suitable address lines 44 for addressing a particular sensing assembly 5 and transmitting of the voltage signal through the multiplexer 41 to multiplexer 43, which similarly has input address lines 45 for coupling the lines 42 in sequence to an output line 46. The multiplexer 43 also includes inputs connected to the reference sensing unit 25, which reading is coupled to the output line 46 in each sequence. Thus, each of the voltages generated as a result of the infrared radiation is sequentially transmitted to the output line 46.

Each of the signals is suitably shaped and amplified in a suitable amplifier circuit or unit 47, which is readily and commercially available. The illustrated circuit includes a pair of cascaded operation amplifiers, the first of which includes an offset network 47a. The amplified voltage signal is applied to an analog to digital converter 48 which converts each analog signal into a suitable multiple bit binary number or word suitable for processing in a suitable microprocessor. The successive approximation type analog to digital converter 48 is of any suitable construction and is shown as a well known chip having feedback circuit 48a of a conventional construction. Suitable starting and clock input controls from the computer enable the analog and digital converter 48 and initiate the reading and conversion cycle. Thus, each voltage signal is converted into an eight bit binary word which is coupled through an interfacing circuit chip of unit 49 to a microprocessor system 50 FIG. 7.

The illustrated microprocessor 50 includes a central processing unit (CPU) 51 shown as the well-known MSC6502 chip manufactured and sold by MOS Technology, Inc. The microprocessor system 50 includes a read only memory 52 in which the basic control as well as the thermal diagnostic programs are stored and a random access memory 53 for storing and processing the voltage signals in accordance with the programs. The illustrated processor system 50 thus includes a set of processor and system control lines for initiating and sequencing the operation of the system and for synchronizing of the several functions and processing sequences. A bidirectional data bus 54 is coupled through data bus drivers 55 to the data inputs for transmitting and receiving of data to and from memories 52,53, and I/O components such as the A/D converter interface unit 49, the age entry dial units 9 and the readout or display unit 8. Data bus 54 is an eight line bus for transmitting of eight bit data words. In addition, the processor unit 51 includes a set of address lines, which in the illustrated embodiment includes 16 individual address lines. The address lines are interconnected through suitable bus drivers 56 to a sixteen line address bus 57 coupled to the memories and the I/O components for appropriately addressing of the several devices during the processing cycle.

The processor unit 51 also includes control lines 58 coupled through suitable logic circuits for sequencing of the several routines and particularly for reading of the sensors, processing said signals, storing of the processed signals and then calculating of various parameters from which the numeric display value is calculated and displayed.

The start or reset key 12 controls 9 switch 60 connected in a pulse circuit 61 for signaling of the control lines 58 including a reset line 6/a to reset the processor 51 for starting of a processing cycle from the first instruction in memory 52.

The read only memory (ROM) 52 is shown as an eraseable read only memory in which the program is stored for controlling of the system. The memory 52 includes a plurality of 2708 chips 62 which are connected to the common data bus 54 through suitable buffer drivers 63, shown as 8T96 chips. The several chips 2708 are also coupled to the address lines 0 through 9 of the address bus 57 through suitable buffer driver 64 shown as 8T95 buffer chips. A chip selection decoder 65, shown as an 74LS138 chip, includes eight output select lines 66, connected one each to the 8 ROM 2708 chips. The decoder 65 includes 3 address inputs connected to address lines 10, 11 and 12 of the address bus 57 and a further input "coded" to the address lines 13, 14 and 15 through a NAND gate 67 such as a 74LS10 chip. The several inputs are decoded by the decoder 65 to selectively enable one of the 2708 chips of ROM 52. The output of the NAND gate 67 is also connected by a signal line 68 to enable the buffer drivers 63 and 64 interconnected between the ROM inputs and the ROM address and data buses 54 and 57 to enable the corresponding drivers whenever the ROM memory has been selected for communication with the processor.

The RAM memory 53 is shown including eight AM9140E chips 69 with address lines 70 coupled to the address bus 57 and particularly lines "0-11". A selection logic circuit 71 includes a NAND gate 72 connected to three address lines and an OR gate 73 connected to the output of the NAND gate 72 and address line 13. The chips 69 include the usual control inputs and input and output lines coupled to the data bus 54 by a pair of bidirectional buffer drivers 74, also shown as 8T28 chips.

Referring to FIG. 6, the data interfacing unit 49 is shown as a known MCS6520 chip which includes a plurality of control lines 75 coupled to the corresponding lines and sequence control of the microprocessor 51 as subsequently described. The interfacing unit 49 includes a plurality of interfacing lines, including a group or set of 8 data input lines 76 and control lines 77 connected to the A/D converter 48 for activating the latter and reading the converted binary numbers. The interfacing unit 49 include group or set of multiplex address lines 78 and 79 defining the multiplex selection address lines and connected to the input lines 44 and 45 of the multiplexers 41 and 43. A driver 80, shown as an 8T95 chip, is shown coupling multiplex address lines 78 to the multiplexer 41. Finally interfacing unit 49 includes bidirectional input lines coupled to receive and transmit data and coupled to receive and transmit data coupled to the microprocessor system data bus 54 by suitable buffer drivers 81. The digitized sensor voltage signals are thus read by the processor unit 51 and stored in the RAM memory unit 53.

The processor unit 51 selectively enables the several components by addressing a selection decoder 81 shown as a 7442 chip, having three input lines 82 connected to the address lines 13, 14 and 15 of the address bus 57. Decoder 82 has four output lines 83. The first output line is connected to enable the interfacing unit 49, and conjointly with the read/write control line of lines 75 is connected by a logic circuit 84 to enable the drivers 81.

The patient's age is introduced using a pair of conventional series 300 digiswitches 85 settable by thumbwheels 9, having 10 dial positions and providing an output numbers in BCD. The pair of switches provided include a most significant digit and a least significant digit. The binary output signals of these switches are connected by a pair of buffers 86 to the data bus 54. The buffers 86 are shown as 8T09 chips having the enabling inputs connected to the second output of lines 83 of the decoder 82.

The display unit 8 includes four 7 segment LED units 87. Latch units 88 connect segment input lines to the data bus 54. The latch units 88 have selection inputs connected to the third and fourth output lines of the address decoder 82.

In use, the patient is located in front of the arrays units 3 and 4, which are then vertically and horizontally properly aligned with the patient. The system operation is initiated by activation of the start or reset switch 60. The processor 51 resets to the initial or starting program address of the programmed ROM memory 52 which provides the usual housekeeping routine to initialize all of the necessary elements. The program then proceeds to sequentially read the total of the 129 sensor assemblies 5 and 51, 64 sensors for each of the breast scanning units and the reference sensor assembly 5a for determining the reference temperature in the sternal area. Each sensor voltage, which is directly proportional to the average temperature of the breast portion aligned with the mirror 35, is sequentially read through the multiplexing system and digitized by the A/D converter 48. The numbers are converted by the processor 51 into a BCD number which is stored in the RAM memory 53. The numbers are preferably stored in two floating point arrays, identified as the left and right arrays. In accordance with known conventions, the floating point number may consist of the five binary bytes in which the first byte identifies the most significant bit while the second, third and fourth bytes include the mantissa digits of the BCD numbers and the fifth byte includes the exponent. Each point number and reference temperature number is adjusted by the processor 51 such that the range of input values lies between 0 and 511, and then the 511th complement of all numbers is taken. A value of "0" defines a point that is hot while a value of "511" defines a point that is cold. Each temperature point in each array is considered cold if its temperature number is greater than the reference temperature and hot if its temperature number is smaller than the reference temperature number. The total temperature pattern is rapidly determined and stored as a pattern of digital numbers in the memory 53 in relatively short period of time and particularly with a relatively inexpensive and reliable scanning apparatus.

After storage of all of the data, the microprocessor executes a series of pattern recognition programs to develop an automatic diagnosis, and finally to display in numeric form the result of such diagnosis in encoded numeric form upon the display.

Generally the invention may employ the several individual parameters more fully developed in the previously referenced Ziskin Article, a table of which is reproduced below:

TABLE I
ELEMENTAL FEATURES

| Name | Parameter Number |
| --- | --- |
| Hottest gridel on left | P8 |
| Hottest gridel on right | P9 |
| Horizontal "shift" between left and right hottest gridel | P10 |
| Vertical "shift" between left and right hottest gridel | P11 |
| Hottest region on left | P12 |
| Hottest region on right | P13 |
| Areolar temp. on left | P20 |
| Areolar temp. on right | P21 |
| Reference temperature | P5 |
| Average temperature of left breast | P26 |
| Average temperature of right breast | P27 |
| Average temperature of all hot regions on left | P18 |
| Average temperature of all hot regions on right | P19 |
| Total hot area on left | P16 |
| Total hot area on right | P17 |
| Highest $P^2/A$ value on either side | P24 |
| Lowest $P^2/A$ value on either side | P25 |
| Number of hot regions on left | P22 |
| Number of hot regions on right | P23 |

The above parameters are elemental parameters based on the previously identified articles from which various analyses and comparisons are developed, as more fully developed hereinafter, to produce a suitable indication of the probable presence of breast cancer.

The elemental features or parameters of the above table are calculated by suitable processing algorithms for each of these parameters, such as the following which parameters are similar to those described by Ziskin and a suitable program for processing of each is shown in Appendix "A" of record. The program employs the KIM MATH package provided with the 6502 microprocessor.

Hottest Gridel on Left (P8)

This parameter indicates the temperature of the hottest single gridel on the left side. The processor is programmed to search the left array memory for the minimum value. The address of the left side array is set in the appropriate registers using SADLST and SADLSY routines. The first number of the array is moved into RY register by using the KIMATH routine PLOADY and the second number is loaded into RX register by using the KIMATH routine PLOADX. The ADD routine is called to compare the two members and the smallest absolute value on return is place in RY register. The rest of the numbers in the array are compared with the running minimum number. When all the 64 numbers are compared, the RY register has the smallest number in the array, which is copied into the RZ register. The KIMATH routine PSTRES is used to store the number from RZ register into the P8 register. This routine also converts from the computational format of RZ (18 bytes) into the packed format of P8 (5 bytes). The algorithm for the left side is P8=Min. LST(i), i=0 to 63

Hottest Gridel on Right (P9)

This parameter is similarly found by searching the right side (RST) array.

Symmetry Parameters (P10, P11)

These two parameters measure the symmetry in the relative anatomic placement of the hottest gridels on the two breasts. P10 is the horizontal shift while P11 is the vertical shift between these two hottest gridels. The location in the matrix of the hottest gridel in each side is found. LHGL(1) is the location of the hottest gridel on the left and LHGR(1) is the location of the hottest gridel on the right. Also the following variables of interest are calculated:

CL is the column number of the hottest gridel on the left and the value in the right most 3 bits of LHGL(1)

RL is the row number of the hottest gridel on the right and is found by shifting LHGL(1) right by 3 bits.

CR is the column number of the hottest gridel on the right and the value in the rightmost 3 bits of LHOR(1)

RR is the row number of the hottest gridel on the right and is found by shifting LHRG(1) right by 3 bits.

These four variables for the $8 \times 8$ matrix have a range of 0 to 7 and P10 and P11 are calculated therefrom by the following algorithm:

$$P10 = |(7-CL)+CR|$$

$$P11 = |RL-RR|$$

The parameter P10 has a range of 0 to 14 while parameter P11 has a range of 0 to 7.

Areolar Temperature on left and right sides identified as parameter P20 and P21 are determined by similar algorithms, which stated for the left side is $$P20 = (LST(27)+LST(28)_4)+LST(35)+LST(36)$$

The Average Temperature of the left and right are similar by calculated, as parameters (P26) and (P27)

This average temperature is that of all 64 gridels on the respective side. The algorithm for the left side is $$P26 = \sum_{i=0}^{63} LST(i)/64$$

Hottest Region on Left and Right (P12, P13)

P12 is given by the hottest set of connected gridels or the left. It is calculated by finding the minimum ratio (max temperatures) of the sum of all connected gridels in a region divided by the number of hot points in the region. After the Connection Algorithm, given below, is run for the left side, it is given by MTEMP(5). MTEMP is copied to P12. The parameter (P13) for the right side is then determined in a similar manner and stored in P13.

Connection Algorithm

The connection algorithm is used to find various hot regions in the respective sides. A hot region is defined as a collection of connected hot gridels. Two hot gridels are said to be connected if a continuous line can be enscribed between them which traverses only over hot gridels.

First of all, a dummy array is generated in the routine GDARR. The dummy array identified as SDA(i), i=0 to 99 consists of hot and cold points. For each point in the LST or the RST arrays, the gridel temperature is subtracted from the reference temperature. If the result is negative, the point is considered cold and '00' is stored in the corresponding SDA location. Otherwise x'80' is stored indicating that the point is hot. There are only 64 valid points in the SDA array which correspond to the LST or the RST arrays i.e. 11-19, 20-24, 31-39, 41-49, 51-59, 61-69, 71-79, 81-89. All other points from 0 to 99 are only dummy points and are considered cold.

Connection Algorithm Flowchart

The flowchart for the connection Algorithm is given in FIG. 1, (attached as a part of the Appendix). The SDA array is searched/scanned from 0 to 99 for a hot point. The perimeter of the first hot point is calculated in the routine CALPER. If SDA(i) is the point being assigned in the following array:

| | | |
|---|---|---|
| i − 11 | 8−10 | i − 9 |
| i − 1 | SDA(i) | i + 1 |
| i + 9 | i + 10 | i + 11 | the perimeter P is given by:

$$P = 2\{SDA(i-1) + SDA(i+1) + SDA(i-10 \pm SDA(i+10)\} + \{SDA(i-11) + SDA(i+11) + SDA(i-9 \pm SDA(i+9)\}$$

where SDA i=0 if it is hot, and =1 if it is cold. All other points in the SDA array are scanned and perimeters of other hot points which are immediately adjacent to the first point are calculated. Since the SDA array was scanned in sequence 0 to 99, there may be additional neighbors to newly assigned points in the region, hence a number of passes through the SDA array are made until no more meighbors are located for that region. All points which are assigned are masked uniquely by storing the perimeter or'ed with the number x '40' in order to make sure that there is no conflict with assignable points (s'80'). The higher P2/Q ratio and the lowest P2/Q ratio is maintained by comparing new values for each region with the previous maximum and minimum values (P24 and P25). When the connection algorithm is run for both the left and the right sides, P24 and P25 have the maximum and the minimum P2/A ratio respectively.

Total Hot Area on Left and Right (P16, P17)

This parameter is equal to the number of hot gridels on the respective sides. The number of hot gridels on each side is calculated by counting the number of hot points in the SDA array. All points in the SDA array which have x'80' are hot points. Besides the parameter P16 in the floating point format, a binary count of the number of hot points is accumulated in HGRC(i), for use in the connection algorithm. Also the sum of all hot point temperature is accumulated in STEMP(5).

Average Temperature of the hot regions of left and right sides are (P18, P19)

P18 is the average temperature of the entire hot region on the left side. It is calculated by dividing STEMP(5) by parameter P16 and stores as parameter P18. The parameter P19 is similarly calculated and stored using parameter P17.

Number of Hot Regions on Left and Right (P22, P23)

R(5) has the number of hot regions on left after the connection Algorithm is run for the left side.

After all of the elemental features set forth in the above table have been calculated and the results stored in memory, compound parameters calculation are developed in a straightforward manner. In the present embodiment of the invention, thirteen compound parameters corresponding to selected parameters set forth in the Ziskin article are employed as follows:

| | |
|---|---|
| B1 = patients age, same as P4(age) | |
| B2 = ABS(P17 − P16) | Diff. in no. of hot gridels |
| B3 = ABS(P9 − P8) | Diff. in no. hottest gridel Temp. |
| B4 = ABS(P21 − P20) | Diff. in Average Aerolate Temp. |
| B5 = ABS(P27 − P26) | Diff. in Average Temp. |
| B6 = ABS(P25 − P24) | Diff. in $P^2$/A ratios |
| $B7 = \dfrac{\text{Min (P8, P9)}}{P5}$ | Ration of hottest gridel to Reference |
| B8 = Max(P16, P17) | Largest hot areas |
| $B9 = \dfrac{\text{Min (P26, P27)}}{P5}$ | Temp., normalized hot breast |
| B10 = SQRT(P10)$^2$ + (P11)$^2$ | Symmetry shift |
| B11 = ABS(ABS(P23 − P22) − 1) | Diff. in No. of Hot Regions |
| $B12 = \dfrac{(P12 - 256)\,P16}{P22} - \dfrac{(P13 - 256)\,P17}{P23}$ | Diff. in Heat Emission |
| $B13 = \dfrac{P8}{P26} - \dfrac{P9}{P27}$ | Diff. in Temp. Ratios |

As in the article, in addition to such compound parameters the patient's age is introduced as a parameter. As noted in the article other parameters could be developed and employed.

Thus with all of the parameters available the combined effect of these parameters are summated in an appropriate program of pattern recognition to determine the positive or negative breast cancer diagnosis. The numerically related condition or state number (Z) is calculated based upon the combined effect of the 13 compound parameters. The algorithm is $$Z = \sum_{i=1}^{13} A_i B_i$$

wherein Ai's are the weights assigned to each parameter. The values of these weights which have been employed are:

| | | |
|---|---|---|
| A1 = 1.0, | A2 = .1, | A3 = .4 |
| A4 = .04, | A5 = .1, | A6 = .03 |
| A7 = 10, | A8 = .1, | A9 = 10 |
| A10 = 2, | A11 = −2, | |
| A13 = −80 | | |

The above Z-value program is a direct routine program which can be readily provided by those skilled in the art. The Z-value or number is calculated relative to the number 500 in accordance with the previous number manipulation and as a result, only positive values are obtained. This value will be a number ranging from 0 to 160. To display the A value the exponent Z+4 is first checked to determine if the value is 2. If yes, the two most significant digits are displayed from the Z+1 and the two least significant digits are displayed from Z+2.

If the exponent Z+4 is not 2, but is 1 or 0, the Z+1 and the Z+2 bytes are shifted to the right by either 4 or 8 bits respectively and then displayed. The processor 51 is thus programmed to first determine the number to be displayed and then the Led display 8 is addressed for displaying of the appropriate digital number. The display is a number which is directly related to the diagnostic result providing a reliable indication of the positive and negative cancer diagnosis. The multiple digit number is employed to indicate not only the positive or negative results but the degree of certainty of the diagnosis since many diagnosis are not a definite yes or no but may have various degrees of probability.

All of the components employed in the physiological diagnostic instrument of this invention as disclosed in the above embodiment are presently commercially available. The construction of the apparatus does not require any unusual or sophisticated arrangements. The illustrated embodiment of the invention thus provides a highly satisfactory apparatus based on proven programs of analysis providing a highly reliable screening result.

Although the illustrated embodiment of the invention employs infrared radiation emitted by the surface of the patient, other forms of radiation could of course be employed.

Various modes of carrying out the invention are contemplated as being within the scope of the following claims particularly pointing out and distinctly claiming the subject invention.

I claim:

1. A physiological thermographic detection apparatus comprising first and second multiple sensor array means each defining a sensing area, said arrays each including a plurality of individual thermally responsive units located in a selected pattern and developing individual signals related to the thermal state of the body of an aligned patient, a thermally responsive reference unit, support means, mounting means securing said array means to said support means and including adjustment means for independently positioning each of said arrays relative to each other and with respect to said reference unit, a digital memory means, reading means for recording of the individual signals in said memory means, means for processing of said signals in accordance with a spatial pattern recognition program within each array and in one array relative to the other and in the first and second arrays relative to said reference unit to produce an automatic determination of the significance of said signals, and means for displaying of an encoded signal indicative of the diagnostic result of the pattern recognition process.

2. The apparatus of claim 1 wherein each of said thermally responsive units are mounted in a common plane which is adapted to be located in close spaced relationship to a human body and each of said units includes a thermal sensor and an energy collection means associated with each sensor for collecting of the energy over the aligned portion of the patient's body and concentrating of such energy upon said thermal sensor to generate an analog signal proportional to the temperature of the aligned portion.

3. In the apparatus of claim 1 wherein each of said thermally responsive units includes a thermally activated sensor and an optical reflector means located in aligned spaced relation to the sensors and mounted in spaced alignment therewith, said mounting means for said array means including vertical locating means for locating of the first and second matrix in a corresponding vertical position and horizontal locating means for relative horizontal positioning of the first and second array means relative to each other and into alignment with selected body portions of a patient, and circuit means connected to said first and second array means for selected connection of said sensors to said memory means.

4. The detection apparatus of claim 1 wherein said means for processing of said signals includes a microprocessor input reading means connected to said responsive units for separately reading of each of said analog signals and digitizing said signals and having address means for sequentially actuating said reading means to read the signals of said thermally responsive units and store said digitized signals in predetermined locations in said memory means in accordance with the first and second array means and the reference unit, and said microprocessor having a programmed processing means connected to said addressing means and to said memory means for locating selected maximum and minimum stored signals in each of said arrays and for calculating biologically related parameter numbers based upon said maximum and minimum stored signals within each array and in one array relative to the others and relative to the reference unit and processing the summated biologically related parameter numbers and generating a related number as said encoded signals.

5. The apparatus of claim 4 wherein each of said array means each includes a similar matrix of said thermally responsive units, each of said responsive units including a thermal sensor and an associated individual optical member for collection of energy and concentration of such energy upon the associated thermal sensor for individual separate measurement of the thermal characteristic aligned with the optical member, and said adjustment means providing for relative universal spacial movement of the arrays relative to each other in a common plane for locating of said arrays with respect to spaced areas of the individual patient for any desired location of the individual arrays.

6. The apparatus of claim 5 wherein said reference unit includes a separate sensor for alignment with the region between the two arrays for establishing a reference temperature number, said reference unit being attached to one of said arrays for simultaneously positioning therewith, and means for storing said reference temperature number in said memory means.

7. The apparatus of claim 6 wherein each of said arrays includes at least 64 individual sensors and associated optical reflector members arranged in an 8×8 inch grid, each of said sensors developing an analog signal proportional to the thermal energy, said reading means including means for converting of said analog signal into digital signals for storage in said digital memory, and said microprocessor being connected to said memory means and including address means and processing means for processing of the stored signals in accordance with said pattern recognition programs to produce an automatic diagnostic result based on mathematical computations employing the stored signals.

8. A physiological thermographic detection apparatus comprising first and second multiple sensor array means, means for separately and independently positioning each of said arrays relative to each other and relative to a patient, each array means defining a sensing area and each array means including a plurality of individual sensor units located in a selected and fixed pattern and developing individual analog voltage signals related to the infrared radiation of the body of an aligned patient, a multiplexing means connected to said sensor units and having an output means, a digital memory means, an analog-to-digital converter connected to said output means, means for actuating said multiplexing means to sequentially read said analog voltage signals and means for recording of the individual signals in said memory means, a microprocessor means for processing of said stored signals to determine the location and various temperature characteristics of various areas in accordance with a spacial pattern recognition program of normal and abnormal temperatures within each array and in an array relative to the other array, means to assign different numerical significance to the determined parameters and to summate the individual determinated parameters for the various areas and thereby produce an automatic diagnostic result of the significance of said signals, and a readout means for displaying of an encoded alphanumeric display of the diagnostic result of the pattern recognition process.

9. The apparatus of claim 8 wherein each of said thermally responsive units senses the radiation over the aligned portion of the patient's body and produces an analog signal proportional to the total radiation over such area.

10. The apparatus of claim 9 wherein each of said array means includes a rectangular matrix of said sensor units, each of said sensor units including a radiation sensor and an optical means located in aligned spaced relation to the sensors and mounted in spaced alignment therewith for collecting and concentrating said radiation on the sensor.

11. The apparatus of claim 10 including a separate support for each array means for locating of the first and second matrix in a corresponding vertical position, and means for relative horizontal positioning of the first and second matrix relative to each other and into alignment with selected body portions of a patient.

* * * * *

UNITED STATES PATENT AND TRADEMARK OFFICE
CERTIFICATE OF CORRECTION

PATENT NO. : 4,186,748  Page 1 of 2
DATED : February 5, 1980
INVENTOR(S) : Kenneth J. Schlager It is certified that error appears in the above-identified patent and that said Letters Patent are hereby corrected as shown below:

Column 1, Line 55 — After "body" cancel "," and substitute therefore --- . ---;

Column 3, Line 29 — After "switch" cancel "buttom" and substitute therefore --- button ---;

Column 7, Line 36 — After "of the" cancel "arrays" and substitute therefore --- array ---;

Column 9, Line 8 — After "i=0 to 63" insert --- . ---;

Column 9, Line 48 — T̶h̶e̶x̶c̶a̶l̶c̶u̶l̶a̶t̶i̶o̶n̶ Cancel Calculation "P20=(LST(27)+LST(28)4)+LST(35)+LST(36)" and substitute therefore
$$--- P20 = \frac{LST(27)+LST(28)+LST(35)+LST(36)}{4} ---;$$

UNITED STATES PATENT AND TRADEMARK OFFICE
CERTIFICATE OF CORRECTION

PATENT NO. : 4,186,748
DATED : February 5, 1980
INVENTOR(S) : Kenneth J. Schlager It is certified that error appears in the above-identified patent and that said Letters Patent are hereby corrected as shown below:

Column 10, Lines 35 thru 37, Cancel Calculation "P = 2 {SDA(i-1) + SDA(i+1) + SDA(i-10) + SDA(i+10)} + {SDA(i-11) + SDA(i+11) + SDA(i-9) + SDA(i+9)}" and substitute therefore --- P = 2 {SDA(i-1)+SDA(i+1)+SDA(i-10)+SDA(i+10)} + {SDA(i-11)+SDA(i+11)+SDA(i-9)+SDA(i+9)} ---;

Column 10, Line 46  After "more" cancel "meighbors" and substitute therefore --- neighbors ---;

Column 12, Line 16  After "above" cancel "embodiment" and substitute therefore --- embodiments ---;

Column 12, Line 19  After "illustrated" cancel "embodiment" and substitute therefore --- embodiments --- and after "thus" cancel "provides" and substitute therefore --- provide ---.

Signed and Sealed this

Sixteenth Day of September 1980

[SEAL]

Attest:

SIDNEY A. DIAMOND

Attesting Officer    Commissioner of Patents and Trademarks